US009599579B2

(12) United States Patent
Durette

(10) Patent No.: US 9,599,579 B2
(45) Date of Patent: Mar. 21, 2017

(54) METHOD FOR INSPECTING AN INFRASTRUCTURE, COMPTON SCATTERING INSPECTION DEVICE AND METHOD OF OPERATING THEREOF

(71) Applicant: INVERSA SYSTEMS LTD., Fredericton (CA)

(72) Inventor: Shawn Durette, Yoho (CA)

(73) Assignee: Inversa Systems LTD., Fredericton (CA)

( * ) Notice: Subject to any disclaimer, the term of this patent is extended or adjusted under 35 U.S.C. 154(b) by 0 days.

(21) Appl. No.: 15/231,973

(22) Filed: Aug. 9, 2016

(65) Prior Publication Data

US 2017/0052126 A1    Feb. 23, 2017

(30) Foreign Application Priority Data

Aug. 20, 2015  (CA) ...................................... 2901438

(51) Int. Cl.
*G01N 23/20* (2006.01)
*G01N 23/04* (2006.01)

(52) U.S. Cl.
CPC ..... *G01N 23/20066* (2013.01); *G01N 23/046* (2013.01); *G01N 2223/628* (2013.01); *G01N 2223/646* (2013.01)

(58) Field of Classification Search
CPC ....... G01N 2223/625; G01N 2223/646; G01N 23/046; G01N 23/20066
See application file for complete search history.

(56) References Cited

U.S. PATENT DOCUMENTS

| 4,856,336 | A | * | 8/1989 | Falkevich | ............... | G01N 29/34 |
| | | | | | | 73/598 |
| 5,042,305 | A | * | 8/1991 | Takishita | ................ | B82Y 15/00 |
| | | | | | | 73/625 |
| 7,203,276 | B2 | | 4/2007 | Arsenault et al. | | |
| 2014/0060580 | A1 | * | 3/2014 | O'Donnell | .............. | B08B 9/027 |
| | | | | | | 134/18 |
| 2014/0238136 | A1 | * | 8/2014 | Ten Grotenhuis | . | G01N 29/0654 |
| | | | | | | 73/592 |
| 2015/0377804 | A1 | * | 12/2015 | Arsenault | ........ | G01N 23/20066 |
| | | | | | | 250/393 |

* cited by examiner

*Primary Examiner* — Mark R Gaworecki
(74) *Attorney, Agent, or Firm* — Norton Rose Fulbright Canada LLP; Alexandre Daoust

(57) ABSTRACT

The method is for inspecting an infrastructure having a corrugated pipe at least partially surrounded by soil. The corrugated pipe has a cylindrical wall which is corrugated along a length thereof and forming a longitudinally extending series of corrugations. The method generally has the steps of emitting, outwardly from the interior of the corrugated pipe, a beam of radiation particles directed towards a given voxel positioned beyond an inner face of the cylindrical wall and along a scanning plane parallel to an orientation of individual ones of the corrugations of the cylindrical wall; detecting backscattered photons scattered back from the given voxel and along the scanning plane; and generating inspection data based on the detected backscattered photons associated with the given voxel for use in inspecting the corrugated pipe.

20 Claims, 10 Drawing Sheets

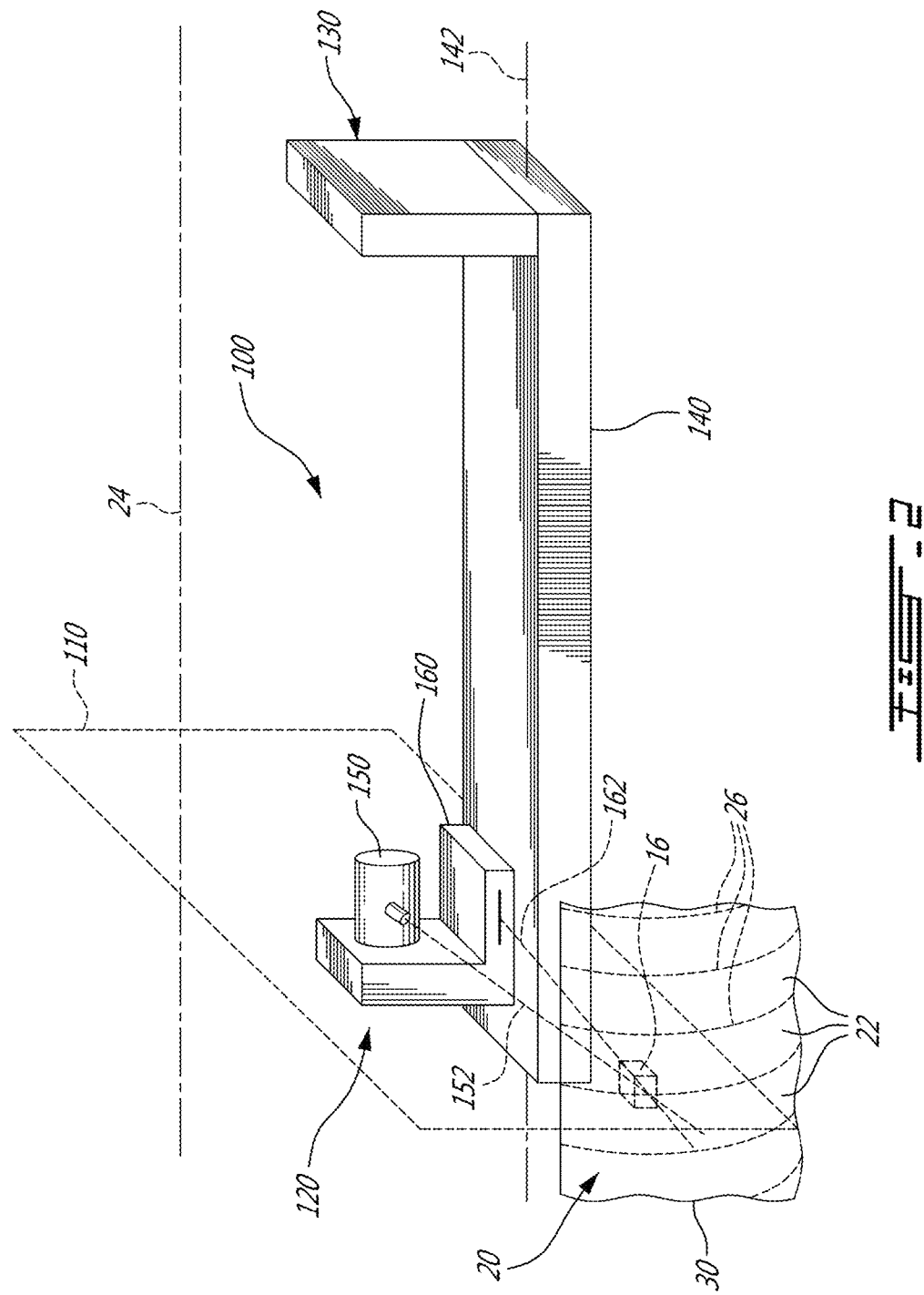

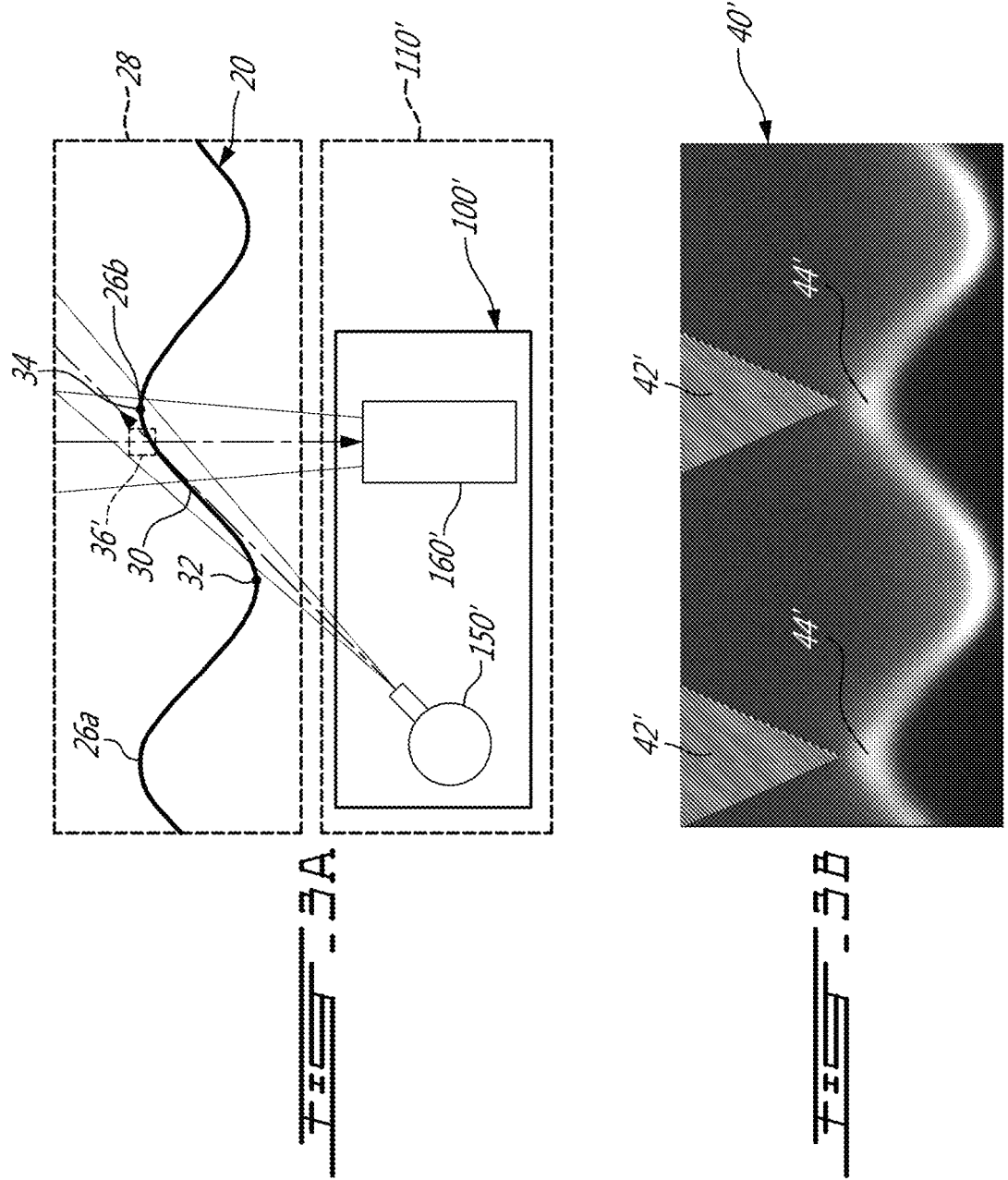

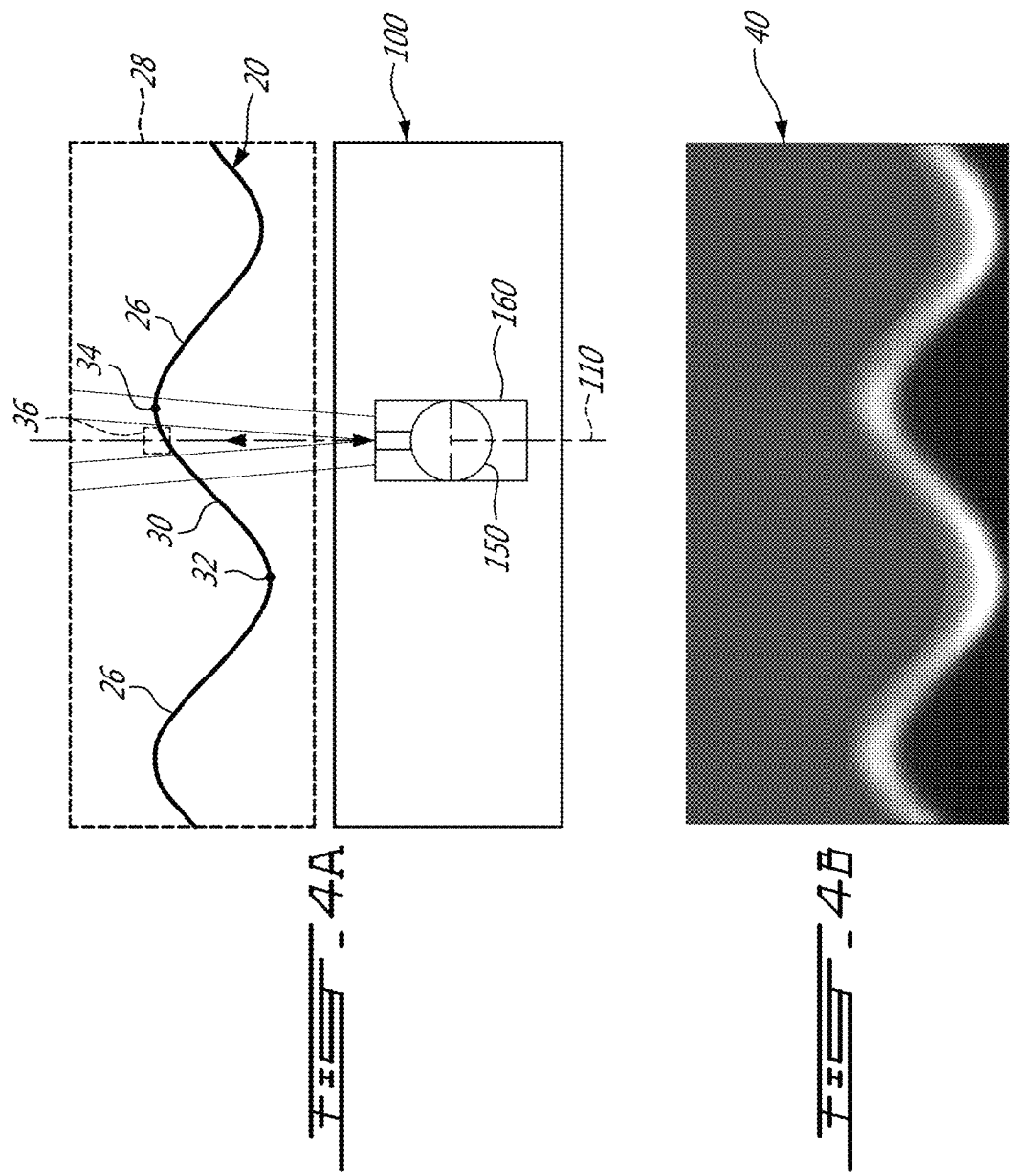

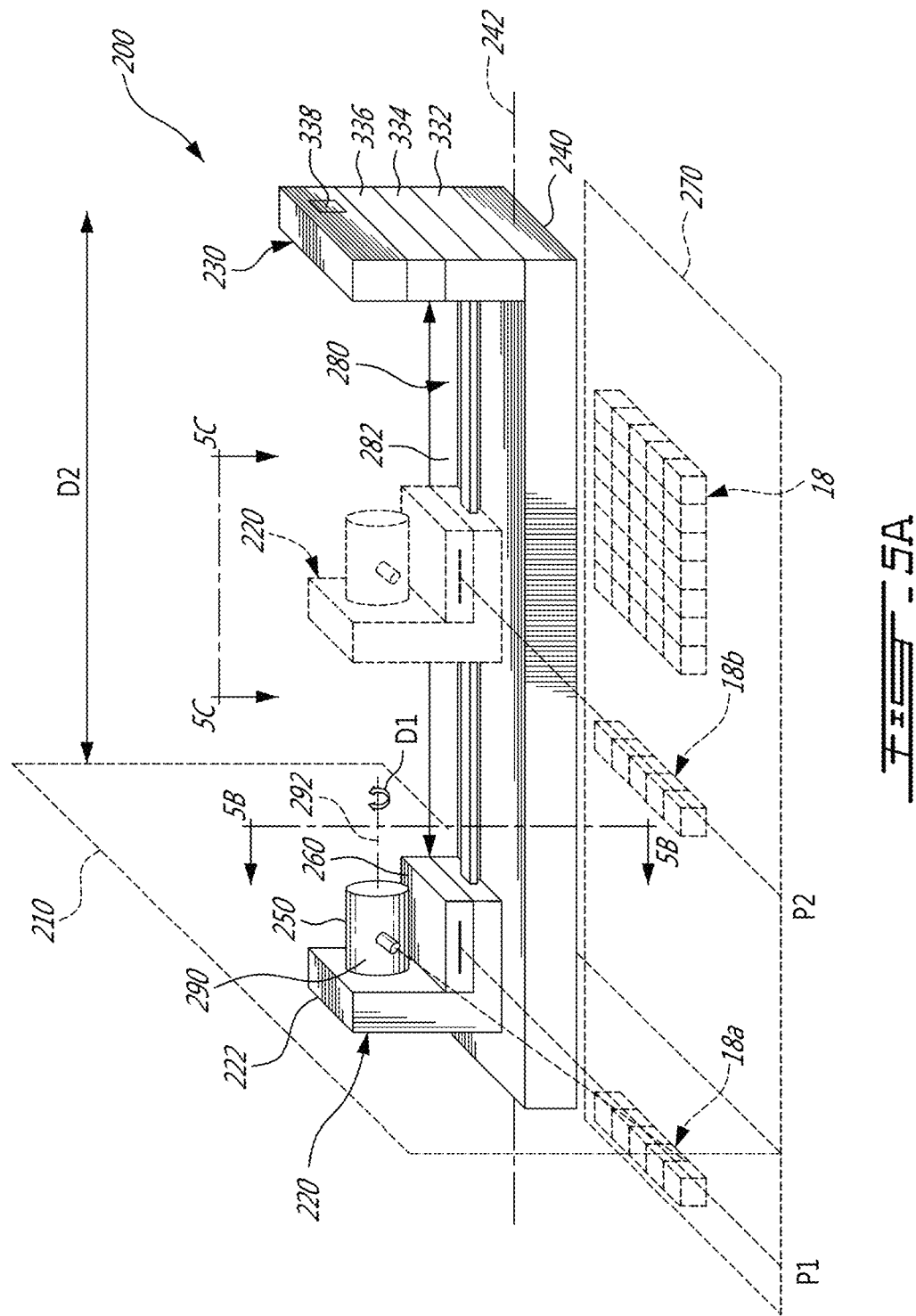

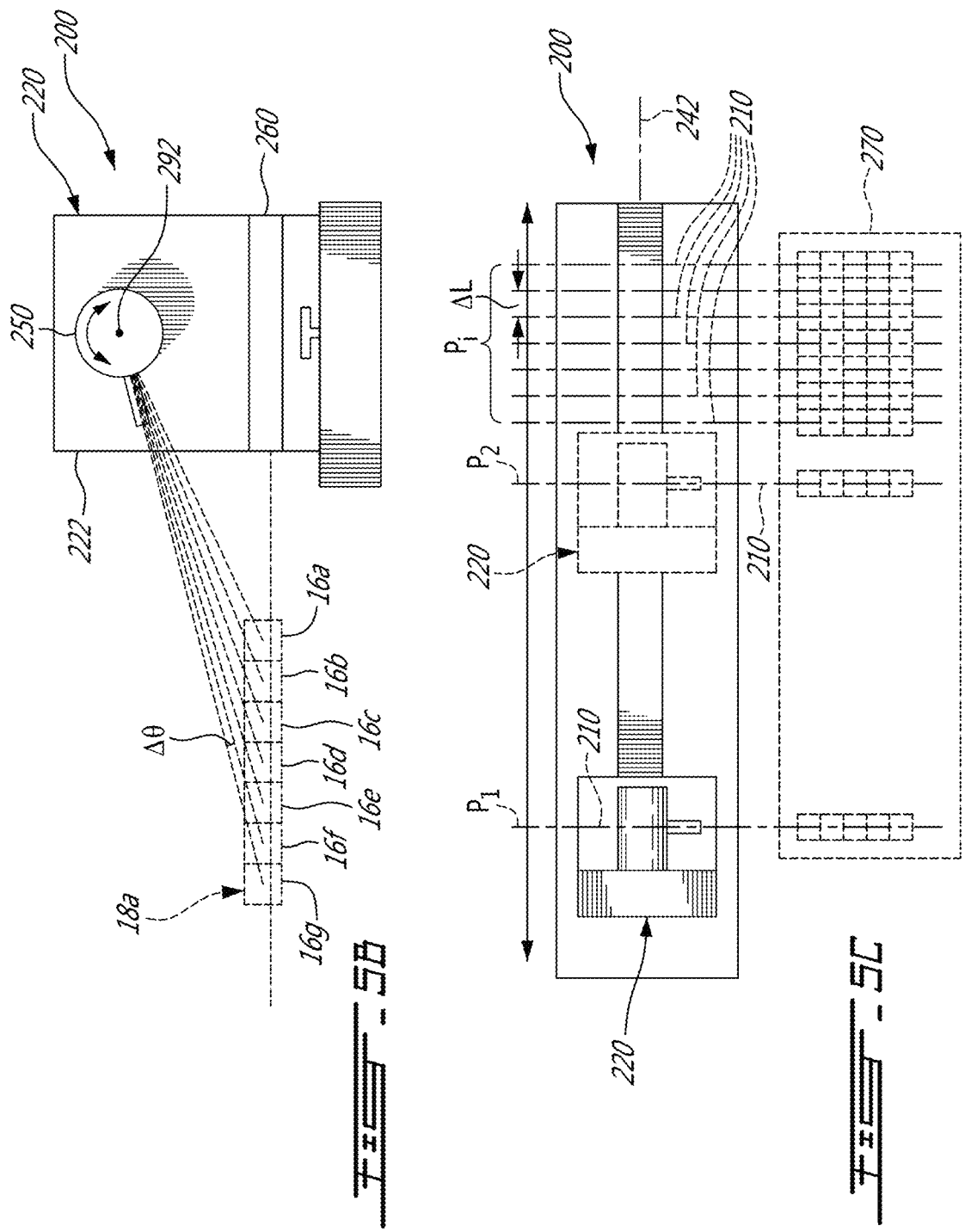

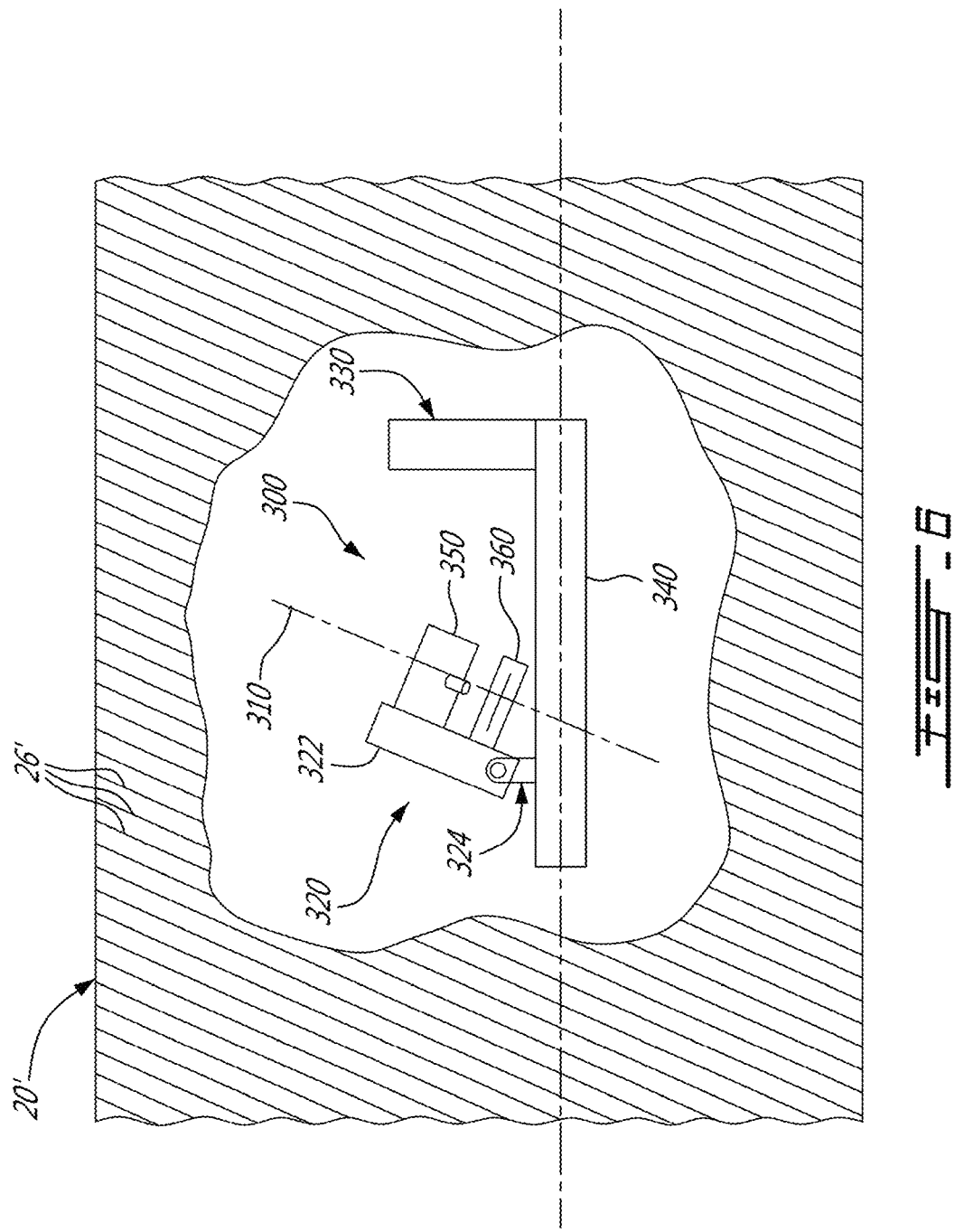

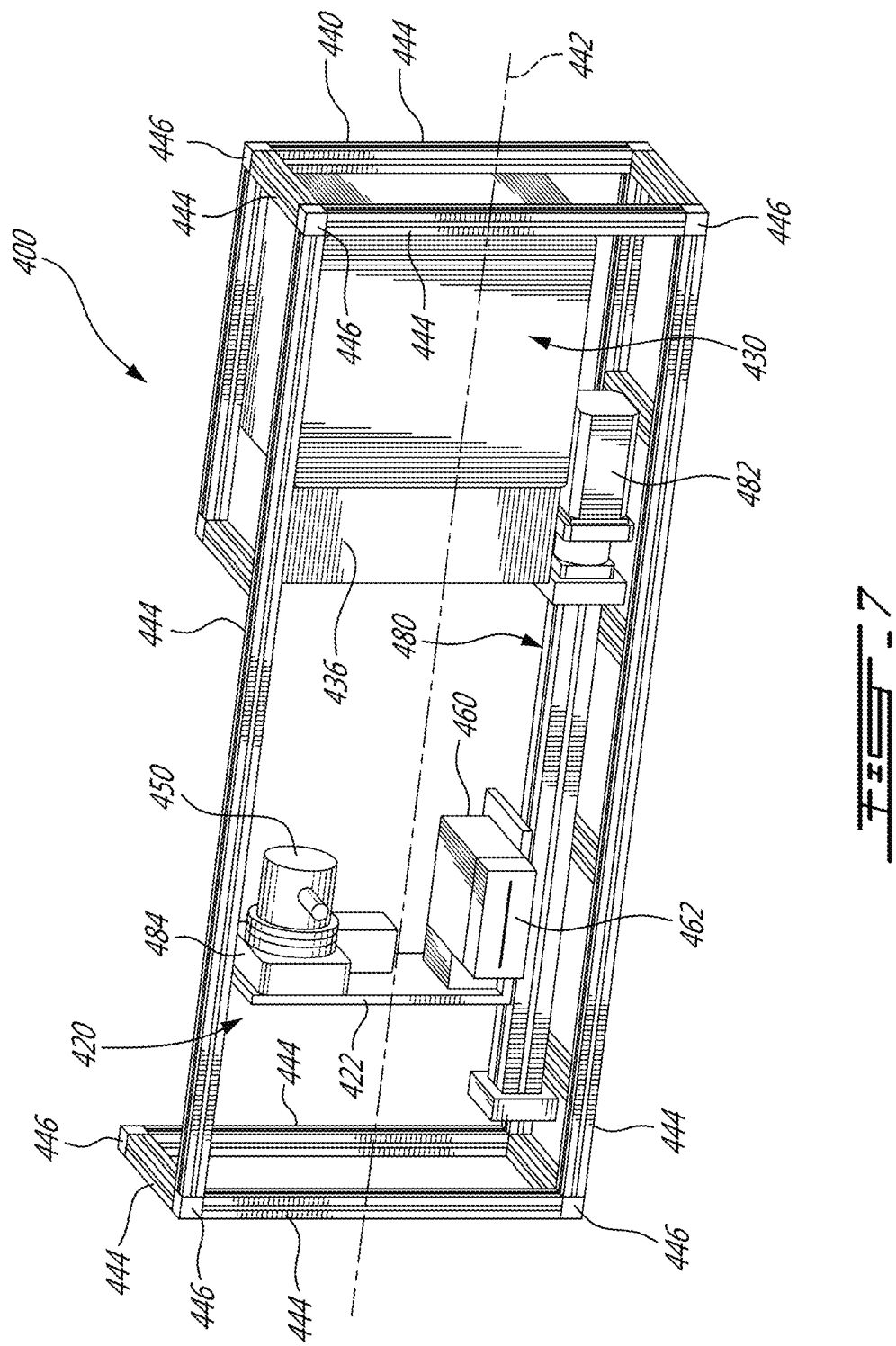

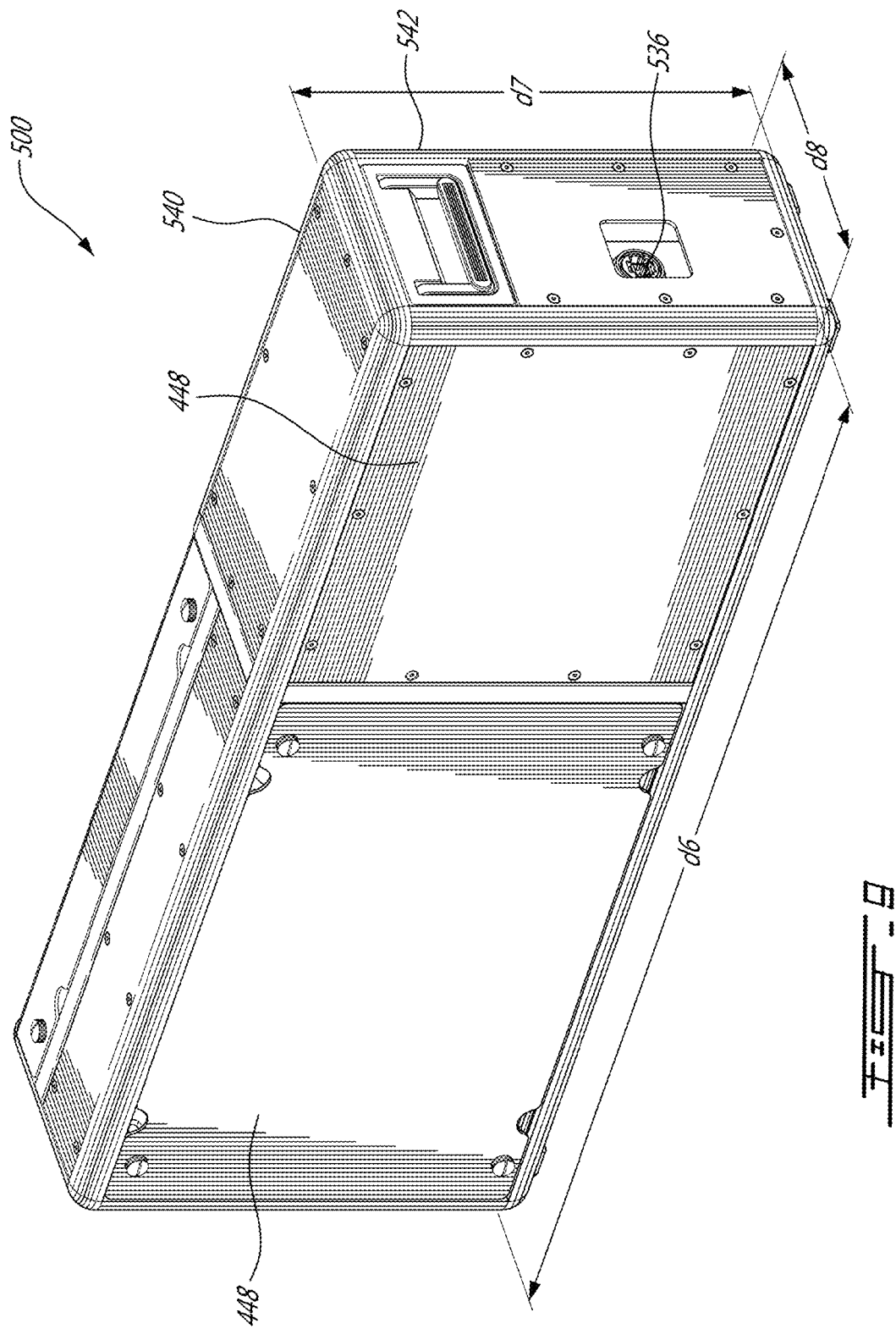

METHOD FOR INSPECTING AN INFRASTRUCTURE, COMPTON SCATTERING INSPECTION DEVICE AND METHOD OF OPERATING THEREOF

FIELD

The improvements generally relate to methods and systems for inspecting corrugated pipes used in infrastructures and more particularly to such methods and systems which use Compton Scatter.

BACKGROUND

Inspecting infrastructure such as culverts, levees, and storm sewers is of relevance in order to address public safety. For instance, such infrastructures can be provided in the form of underground channels allowing passage of water under roadways and are generally obtained by burying a large diameter pipe under soil.

Culverts, levees, and/or storm sewers can deteriorate over time due to, for instance, erosion of the soil surrounding the pipes. As the soil surrounding a pipe gradually erodes, voids can be created between the surrounding soil and the pipe, thus increasing risks of failure (e.g., washout due to flooding). As deterioration of such infrastructure depends on external physical factors, inspecting each infrastructure is key in providing a satisfactory maintenance plan.

Inspection of such infrastructures is typically provided in the form of visual inspection and/or acoustic inspection. There thus remains room for improvement.

SUMMARY

There is provided Compton Scatter (CS) inspection methods and systems for inspecting an infrastructure having a large diameter corrugated pipe, i.e. a pipe having a cylindrical wall including a plurality of corrugations along its length. By aligning the emission of a beam of radiation particles and the detection of backscattered photons together along a scanning plane which is parallel to an orientation of individual ones of the corrugations, it was found that drawbacks associated with the geometry of the corrugation can be addressed.

In accordance with one aspect, there is provided a method for inspecting an infrastructure having a corrugated pipe at least partially surrounded by soil, the corrugated pipe having a cylindrical wall being corrugated along a length thereof and forming a longitudinally extending series of corrugations, the method comprising the steps of: emitting, outwardly from the interior of the corrugated pipe, a beam of radiation particles directed towards a given voxel positioned beyond an inner face of the cylindrical wall and along a scanning plane parallel to an orientation of individual ones of the corrugations of the cylindrical wall; detecting backscattered photons scattered back from the given voxel and along the scanning plane; and generating inspection data based on the detected backscattered photons associated with the given voxel for use in inspecting the corrugated pipe.

In accordance with another aspect, there is provided a CS inspection device for inspecting an infrastructure having a corrugated pipe, the corrugated pipe having a cylindrical wall being corrugated along a length thereof and forming a series of longitudinally extending corrugations, the CS inspection device comprising: a frame adapted to be received against an inner face of the cylindrical wall and having a main axis; a scanning plane parallel to an orientation of individual ones of the corrugations and intersecting the main axis; a scanning module having an emitter of a beam of radiation particles and a detector of backscattered photons being mounted to the frame and being spaced apart from one another in the scanning plane; and a control module operatively connected to the scanning module and configured to operate the emitter and the detector and to process inspection data received by the detector.

In accordance with another aspect, there is provided a method of operating a CS inspection device for use in inspecting an infrastructure having a corrugated pipe, the corrugated pipe having a cylindrical wall being corrugated along a length thereof and forming a series of longitudinally extending corrugations, the method comprising the steps of: determining a circumferential position and a longitudinal position associated with an area under test of an inner face of the cylindrical wall; providing a support structure having first and second opposite support ends at the longitudinal position of the cylindrical wall; positioning the first end of the support structure to the circumferential position and the second end of the support structure at a different circumferential position thereby; and positioning the CS inspection device on the first end of the support structure and against the inner face of the cylindrical wall at the longitudinal and circumferential positions.

It is understood that the corrugated pipe discussed in this disclosure has a large internal diameter. In an embodiment, the internal diameter is greater than 24 inches, preferably greater than 48 inches.

Many further features and combinations thereof concerning the present improvements will appear to those skilled in the art following a reading of the instant disclosure.

DESCRIPTION OF THE FIGURES

In the figures,

FIG. 2 is an oblique view of an example of a CS inspection device for inspecting an infrastructure having a corrugated pipe, shown with a fragmented view of a series of longitudinally extending corrugations, in accordance with an embodiment;

FIG. 3A is a top plan view of a conventional CS inspection device shown during inspection of an infrastructure having a corrugated pipe surrounded by soil;

FIG. 3B is an example of inspection data obtained using conventional CS inspection device shown in FIG. 3A and displayed in the form of a tomogram;

FIG. 4A is a top plan view of a CS inspection device shown during inspection of an infrastructure having a corrugated pipe surrounded by soil, in accordance with an embodiment;

FIG. 4B is an example of inspection data obtained using the CS inspection device shown in FIG. 4A and displayed in the form of a tomogram;

FIG. 5A is an oblique view of another example of a CS inspection device for inspecting an infrastructure having a corrugated pipe, configured for rastering a tomographic plane, in accordance with an embodiment;

FIG. 5B is a cross-sectional view taken along section 5B-5B of FIG. 5A;

FIG. 5C is a cross-sectional view taken along section 5C-5C of FIG. 5A;

FIG. 6 is a fragmented front elevation view of an example of a CS inspection device for inspecting an infrastructure having a corrugated pipe, showing a scanning module pivoted about an axis perpendicular to a length of the corrugated pipe, in accordance with an embodiment;

FIG. 7 is an oblique view of another example of a CS inspection device for inspecting an infrastructure having a corrugated pipe, shown with actuators, in accordance with an embodiment;

FIG. 9 is an oblique view of an example of a frame of a CS inspection device, provided in the form of a transport box, in accordance with an embodiment.

DETAILED DESCRIPTION

Figure 1B:
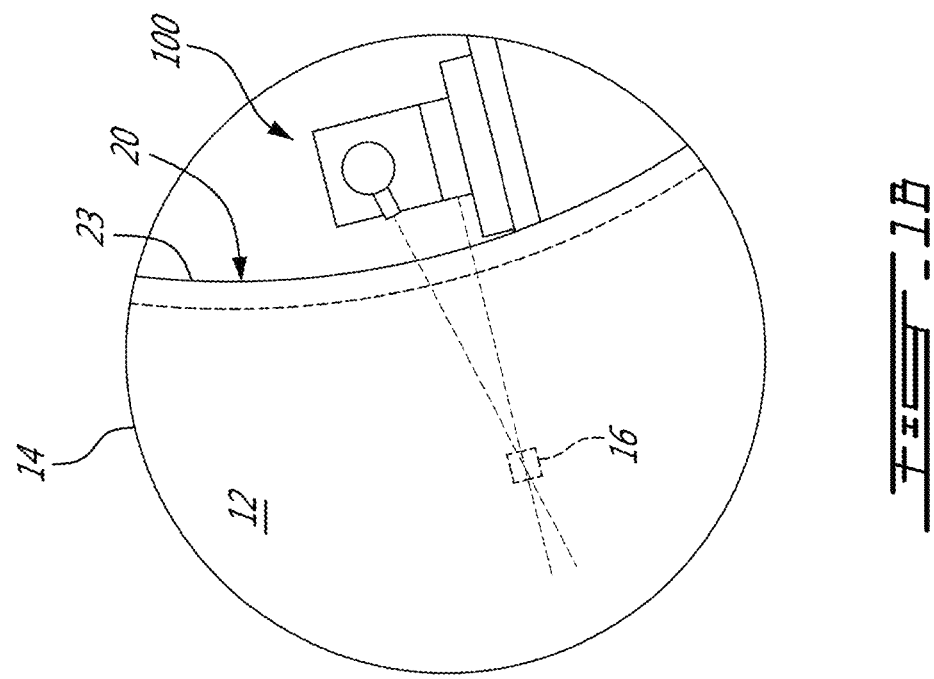
FIG. 1B is an enlarged view of an inset shown in FIG. 1A.
Figure 1A:
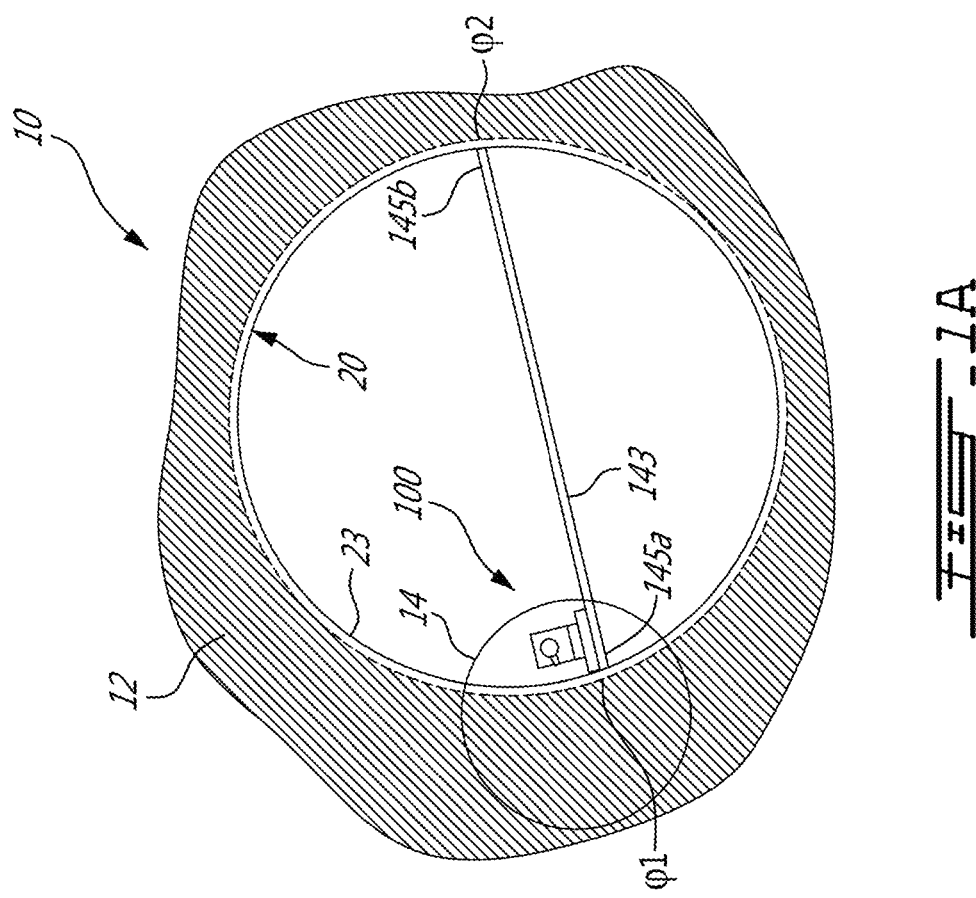
FIG. 1A is a partial side elevation view of an example of a CS inspection device shown during inspection of an infrastructure having a corrugated pipe surrounded by soil, in accordance with an embodiment.

FIG. 1A shows an example of a Compton Scatter (CS) inspection device 100 during inspection, in accordance with an embodiment. The CS inspection device 100 is designed to inspect an infrastructure 10 having one or more corrugated pipes 20 surrounded by soil 12 and to provide inspection data associated with the corrugated pipe 20 and its surrounding soil 12. Examples of such infrastructure are culverts and storm sewers, however, it is understood that other types of infrastructure can have a corrugated pipe 20, and therefore, can be inspected using the CS inspection device 100.

FIG. 1B shows an enlarged view of inset 14 shown in FIG. 1A. As best seen in FIG. 1B, the CS inspection device 100 is directed towards a given voxel 16 (e.g., volume element 16 having a volume of about 4 mm per 4 mm per 4 mm) which is to be inspected by the CS inspection device 100. The given voxel 16 is generally at a position where it is desired to inspect the infrastructure 10, e.g., typically beyond an inner face 23 of the corrugated pipe 20. During use, the CS inspection device 100 is adapted to be received against the inner face 23 of the corrugated pipe 20 so that the CS inspection device 100 can project a beam of radiation particles (i.e. radiation that behaves as a particle), such as gamma-rays, x-rays and neutrons, towards the given voxel 16, outwardly from the interior of the corrugated pipe 20. Backscattered photons, typically referred to as CS radiation, are then detected in order to generate the inspection data. The number of backscattered photons detected is determined so as to obtain a statistically meaningful number of photons while maintaining a practical size, weight and speed for portable use with industrial facilities. The beam can be a pencil beam, a cone beam, and any suitable beam.

Also, it is noted that CS inspection technology has recently been developed, as presented in international patent publication WO 2014/124522, the specification of which is hereby incorporated by reference. CS inspection devices, including CS inspection device 100, can be embodied as Computed Tomography (CT) devices in which case they can be referred to as Backscatter Computed Tomography (BCT) devices. A BCT device typically inspects a plurality of voxels and generates the inspection data which can be displayed in the form of a tomogram, which will be discussed in detail further below. It is noted that the tomogram typically shows a map of density of a section of the infrastructure 10 in order to inspect the infrastructure regarding its density, voids of its surrounding soil, poor compaction of the surrounding soil, integrity and thickness of the corrugated pipe 20, for instance.

For clarity, referring now to FIG. 2, the corrugated pipe 20 can be described as having a cylindrical wall 22 being corrugated along its longitudinal axis or length 24 thus forming a longitudinally extending series of corrugations 26. In the embodiment shown in FIG. 2, the corrugations 26 are circumferential such that each corrugation 26 has an orientation which is perpendicular to the length 24 of the corrugated pipe 20. In cases where the corrugated pipe 20 has a circular cross-section, the corrugations 26 can be annular. In another embodiment, the corrugations 26 are helical and/or inclined (such as shown in FIG. 6) with respect to the length 24 of the corrugated pipe 20 such that each corrugation 26 is inclined with respect to the length 24 of the corrugated pipe 20.

Broadly described, the CS inspection device 100 has a scanning plane 110 which is parallel to an orientation of individual ones of the corrugations 26, a scanning module 120 which is configured to scan the corrugated pipe 20 in a manner parallel to the scanning plane 110, and a control module 130 for operating the scanning module 120 during use. The scanning module 120 and the control module 130 are both mounted to a frame 140 having a main axis 142 which is intersected by the scanning plane 110.

More specifically, the scanning module 120 has one or more emitter of radiation particles 150 (referred to simply as "emitter 150") and one or more detector of backscattered photons 160 (referred to simply as "detector 160") that are spaced apart from one another by a fixed spacing distance (e.g., 15 cm or less) in the scanning plane 110. A fixed spacing distance allows for optimizing shielding of the detector 160 from direct leakage of the emitter 150. It is thus understood that the emitter 150 and the detector 160 respectively emit and detect in a manner parallel to the scanning plane 110 during use. In other words, the emitter 150 has an emission path 152 parallel to the scanning plane 110 along which a beam of radiation particles can be projected, and the detector 160 has a field of view 162 parallel to the scanning plane 110 along which backscattered photons can be detected. Accordingly, during use, the scanning module 120 scans the corrugated pipe 20 along the scanning plane 110 such that the emitter 150 projects the beam of radiation particles along the emission path 152 and parallel to the scanning plane 110 while the detector 160 detects backscattered photons scattered back from the given voxel 16 along the field of view 162 and parallel to the scanning plane 110. For instance, radioactive isotopes used to generate the beam of radiation particles may be provided externally to the emitter 150 and input thereto via a hose or other isotope carrying device.

As will be detailed further below, it is noted that scanning the corrugated pipe 20 along the scanning plane 110, which is parallel to an orientation of individual ones of the corrugations 26, can reduce artifacts in the measurements. For ease of understanding an underlying reason of the artifacts reduction, a comparison of FIGS. 3A-B and FIGS. 4A-B is presented. Accordingly, FIG. 3A shows a conventional CS inspection device 100' and associated inspection data in FIG. 3B while FIG. 4A shows the CS inspection device 100 and associated inspection data in FIG. 4B.

Specifically, FIG. 3A shows that the conventional CS inspection device 100' scans a section 28 of the corrugated pipe 20 along a plane 110' parallel to the section 28, i.e. not parallel with an orientation of individual ones of the corrugations 26. In other words, the conventional CS inspection device 100' has an emitter 150' and a detector 160' which respectively emit and detect along the plane 110'. In this configuration, the conventional CS inspection device 100' typically provides inspection data 40', where the section 28 of the corrugated pipe 20 is imaged. It was noted that, when using the conventional CS inspection device 100', the inspection data 40' systematically had artifacts provided in the form of blind spots 42' near each imaged concave apex 44'. It was found that a cause of these blind spots 42' was that, at some point during the inspection, scanning occurs through a substantially long wall portion 30 of the corrugated pipe 20, typically between convex and concave apexes 32, 34 associated with successive corrugations 26a,b. For instance, when imaging an exemplary voxel 36', located near the concave apex 34, such as shown in FIG. 3A, the emitter 150' projects the beam of radiation particles towards the exemplary voxel 36' and through the length of the wall portion 30 while the detector 160' detects backscattered photons associated with the exemplary voxel 36'. It was found that propagation of the beam of radiation particles through the length of the wall portion 30 was likely interacted with it (e.g., by scatter, absorption) such that the exemplary voxel 36' was not appropriately imaged in inspection data 40', thus yielding the blind spots 42' in the inspection data 40'. Referring now to FIGS. 4A-B, it was found that, by providing a CS inspection device 100 which has the emitter 150 and the detector 160 in the scanning plane 110 which is parallel to individual ones of the corrugations 26, the blind spots were substantially avoided. Indeed, the CS inspection device 100 is configured such that the emitter 150 directs the beam of radiation particles towards exemplary voxel 36, located near the concave apex 34 without propagating through the length of the wall portion 30 of the corrugated pipe 20. Accordingly, the CS inspection device 100 can provide inspection data 40 which are exempt from the blind spots, such as shown in FIG. 4B.

Referring back to FIG. 1A, it is noted that the frame 140 is removably mounted to a support structure 143. As shown, the support structure 143 has two opposite supports ends 145a,b each extending outwardly towards circumferentially positions ϕ1 and ϕ2 of the corrugated pipe 20. In the illustrated embodiment, the support end 145a is adapted to receive the frame 140 of the CS inspection device 100 so that it can be abutted on the inner face 23 of the corrugated pipe 20.

In an embodiment, the CS inspection device 100 is manually operated by a user. In an exemplary method of operating the CS inspection device 100, the user can determine (e.g., using visual inspection and/or acoustic inspection) an area under test which is to be inspected by the CS inspection 100. Once the area under test is determined, the user can determine a given circumferential position ϕ1 and a given longitudinal position associated with the area under test and relative to a cylindrical coordinate system of the corrugated pipe 20. Then, the user can provide the support ends 145a,b of the support structure 143 at the given longitudinal position so as to position the support end 145a at the circumferential position ϕ1 and the support end 145b at another circumferential position ϕ2 chosen to provide sufficient support of the CS inspection device 100 during use. Once the support structure 143 is suitably positioned within the corrugated pipe 20, the user can position the CS inspection device 100 on the support end 145a in order to inspect the area under test. In another embodiment, the method of operating the CS inspection device 100 can be performed by a robot having an articulated arm supporting the CS inspection device 100 along the corrugated pipe 20.

As mentioned above, more than one voxel can be inspected using the CS inspection system 100 in order to generate the inspection data in the form of a tomogram, for instance. Reference is now made to FIGS. 5A-C which show another example of a CS inspection device at 200. The CS inspection device 200 is configured to raster a plurality of voxels 16 positioned in a tomographic plane 270 in order to generate sufficient inspection data for generating a tomogram showing the integrity of the corrugated pipe 20 and the surrounding soil 12.

For instance, FIG. 5A shows the scanning module 220 at a first longitudinal position P1 along the main axis 242 of the frame 240 and at a second longitudinal position P2 along the main axis 242 (see scanning module 220 in dashed lines). Broadly described, during inspection, the CS inspection device 200 translates the scanning module 220 (and the associated scanning plane 210) at the first longitudinal position P1 along the main axis 242 of the frame 240, inspects a first plurality 18a of voxels associated with the first longitudinal position P1, translates the scanning module 220 at the second longitudinal position P2 along the main axis 242, inspects a second plurality 18b of voxels associated with the second longitudinal position P2 and so forth such that a plurality 18 of voxels associated with each of a plurality of longitudinal positions Pi along the main axis 242 are inspected.

More specifically, in this embodiment, the scanning module 220 has a subframe 222 to which is pivotally mounted the emitter 250 via a pivot joint 290. The pivot joint 290 allows the emitter 250 to pivot about a pivot axis 292 which is perpendicular to the scanning plane 210 (see curvilinear bidirectional arrow D1). FIG. 5B shows a side elevation view of the CS inspection system 200 when the scanning module 220 is translated at the first longitudinal position P1. In this embodiment, the emitter 250 is shown to be pivotable at a plurality of angular positions such that each voxel 16a,b,c,d,e,f,g of the first plurality 18a of voxels can be inspected. It can be seen that the angular position is adjusted so that the inspected voxels are deeper and deeper behind the cylindrical wall of the corrugated pipe 20. In this embodiment, each angular position is separate by an angular increment Δθ.

Moreover, referring back to FIG. 5A, the scanning module 220 is slidably mounted to the frame 240 via a rail assembly 280 for moving the scanning module 220 back and forth (see rectilinear bidirectional arrow D2) in a manner parallel to the main axis 242. In this embodiment, the rail assembly 280 has a longitudinal guide rail 282, and the subframe 222 engages into the longitudinal guide rail 282 for sliding the emitter 250 together with the detector 260 along the main axis 242. FIG. 5C is a top plan view of the CS inspection system 200 shown in FIG. 5A and shows the scanning module 220 at the first longitudinal position P1, and at the second longitudinal position P2 (see the scanning module 220 in dashed line). It can be seen in FIG. 5C that as the scanning module 220 is translated at the plurality of longitudinal positions Pi along the main axis 242, the scanning plane 210 is translated at the plurality of positions Pi. In an embodiment, the longitudinal positions Pi are separated by a longitudinal increment ΔL. In another embodiment, the longitudinal translation speed of the CS inspection device 200 can be about 2 cm/s or more.

As shown in this illustrated embodiment and more specifically in FIG. 5A, the control module 230 has a processor 332 for receiving the inspection data and generating tomograms using the inspection data, a computer-readably memory 334 for storing the inspection data, a power supply 336 for powering components of the CS inspection device 200 and a communication port 338 for transmitting the inspection data and/or receiving instructions from a remote device. In another embodiment, the control module 230 has an antenna for communicating the inspection data to a remote device. In another embodiment, the control module 230 has a display for displaying the inspection data in the form of a tomogram. In another embodiment, the control module 230 has an indicator adapted to generate a void alert signal upon determining that section of the infrastructure 10 inspected has a void in the soil surrounding the corrugated pipe which has a volume larger than a given volume threshold (e.g., 25 cm$^3$). It will be understood that the control module 230 can have more or less hardware depending on the embodiments. Moreover, the control module 230 can be adapted to control the sliding movement of the scanning module 220 and/or the pivotal movement of the emitter 250 via one or more actuators, for instance.

It will be understood that the CS inspection device is not limited to inspect corrugated pipes having a longitudinally extending series of circumferential corrugations (perpendicular to the length of the corrugated pipe), such as shown in FIG. 2. Accordingly, FIG. 6 shows another example of a CS inspection device at 300. The CS inspection device 300 is configured to inspect a corrugated pipe 20' having a longitudinally extending series of the inclined corrugations 26' which are each inclined with respect to the length of the corrugated pipe 20'. As depicted, the CS inspection device 300 has the frame 340, the scanning module 320 and the control module 330 mounted to the frame 340. The scanning module 320 has the subframe 322 to which is mounted the detector 360 and to which is pivotally mounted the emitter 350. In this embodiment, in order to adapt the scanning plane 310 to the inclination of the corrugations 26' of the corrugated pipe 20' which is to be inspected, the subframe 322 is pivotally mounted to the frame 240 via a second pivot joint 324. The second pivot joint 324 has a second pivot axis which is perpendicular to the length of the corrugated pipe, and parallel to the scanning plane 310, which allows the scanning module 320 to pivot as a function of the inclination of the corrugations.

FIG. 7 shows an oblique view of another example of a CS inspection device at 400. As depicted, the CS inspection device 400 has a frame 440 which includes a plurality of rectilinear structure members 444 joined to one another via corner joints 446. For instance, the open spaces of the frame 440 can be closed using removable flat walls 448, such as the one shown in FIG. 9. The scanning module 420 is slidably mounted to the subframe 422 of the scanning module 420 via another example of the rail assembly 480. In this embodiment, the CS inspection device 400 has a first actuator 482 mounted to the frame 440 for sliding the scanning module 420 back and forth along the main axis 442 of the frame 440. Still in this embodiment, the CS inspection device 400 has a second actuator 484 for pivoting the emitter 450 in the scanning plane. In this example, the first and the second actuators 482,484 are provided in the form of electric motors.

It is noted that the detector 460 has an aperture 462 provided in the form of a slit which let pass the backscattered photons during inspection. The aperture 462 is shown to extend along the main axis 442 of the frame 440. Other types of apertures can be used, as will be apparent to the skilled reader.

As shown, the CS inspection device 400 has a control module 430. The control module 430 has the power supply 436 such as a battery pack for powering the actuators 482,484 and other electrical components of the CS inspection device 400 (e.g., display, processor, computer-readably memory).

Figure 8:
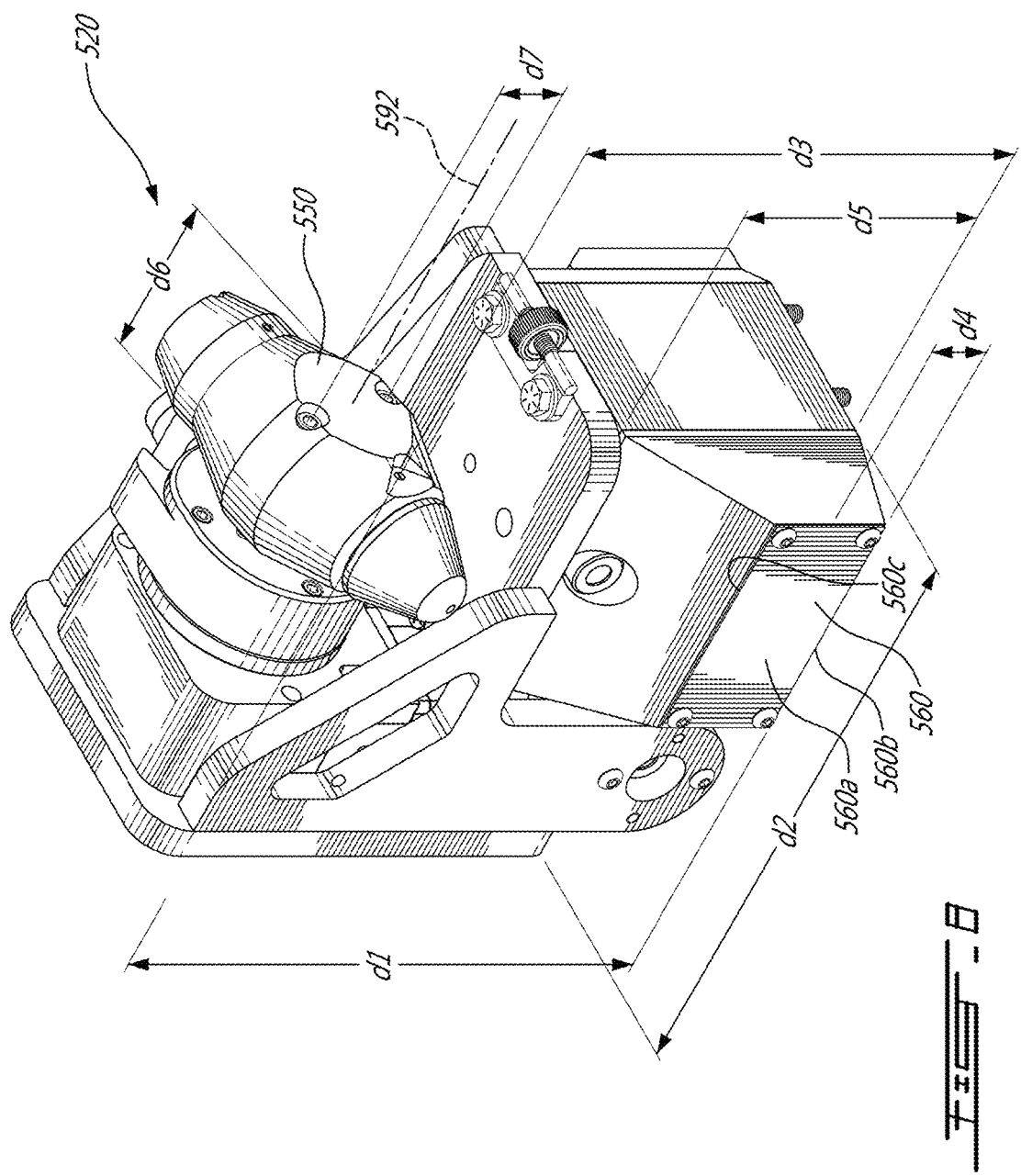
FIG. 8 is an oblique view of an example of a scanning module, in accordance with an embodiment.

FIG. 8 shows an example of a scanning module 520 having an emitter 550 and a detector 560, in accordance with another embodiment. As depicted in this specific example, the scanning module 520 has a height d1 of 8.531 inches, a length d2 of 7.360 inches and a spacing distance d3 of 150 mm between a pivot axis 592 of the emitter 550 and a middle portion 560a of the detector 560. As shown, the detector 560 has a spacing distance d4 of 0.875 inch between a middle portion 560a and a bottom portion 560b, and a spacing distance d5 of 3.819 inches between the middle portion 560a and an upper portion 560c of a housing of the detector 560. Also, the emitter 550 has a head length d6 of 2.250 inches and a head height d7 of 2.750 inches.

FIG. 9 shows an oblique view of another example of the CS inspection device 500 shown with a frame 540, in accordance with another embodiment. In this specific embodiment, the communication port 536 can be provided in the form of an Ethernet cable. As shown, the frame 540 has handles 542 for manual handling of the CS inspection device 500 by a user. In some embodiments, the CS inspection device 500 weight about 90 lbs. In this specific example, the frame 540 has a length d6 of 34¾ inches, a height d7 of 13¾ inches, a thickness d8 of 7¼ inches. [0047] As can be understood, the examples described above and illustrated are intended to be exemplary only. For instance, it is understood that soil includes ground, earth, concrete, minerals, gases, liquids, organisms, etc. It is understood that the corrugated pipe can be a corrugated steel pipe, a corrugated aluminium pipe, a corrugated high-density polyethylene (HDPE) pipe, a recycled corrugated high-density polyethylene pipe (HDPE-R), a polyvinyl chloride pipe (PVC), a profile-wall polyvinyl chloride pipe (PWPVC), or any suitable type of corrugated pipe. The scope is indicated by the appended claims.

What is claimed is:

1. A method for inspecting an infrastructure having a corrugated pipe at least partially surrounded by soil, the corrugated pipe having a cylindrical wall being corrugated along a length thereof and forming a longitudinally extending series of corrugations, the method comprising the steps of:
    emitting, outwardly from the interior of the corrugated pipe, a beam of radiation particles directed towards a given voxel positioned beyond an inner face of the cylindrical wall and along a scanning plane parallel to an orientation of individual ones of the corrugations of the cylindrical wall;
    detecting backscattered photons scattered back from the given voxel and along the scanning plane; and
    generating inspection data based on the detected backscattered photons associated with the given voxel for use in inspecting the corrugated pipe.

2. The method of claim 1, wherein the given voxel being one voxel of a first plurality of voxels positioned in the scanning plane and spaced from one another, the method further comprising:
    performing the steps of emitting, detecting and generating for each other voxel of the first plurality of voxels.

3. The method of claim 2, wherein said performing includes pivoting an emission path of the beam of radiation particles of an angular increment and about a pivot axis perpendicular to the scanning plane for each one of the first plurality of voxels.

4. The method of claim 2, wherein each voxel is positioned in a tomographic plane.

5. The method of claim 1, further comprising:
    translating the scanning plane along the length of the corrugated pipe by a longitudinal increment; and repeating the steps of emitting, detecting and generating for a second plurality of voxels being positioned in the translated scanning plane and being spaced from one another.

6. The method of claim 5, further comprising performing the steps of translating and repeating for a plurality of longitudinal positions each having an associated plurality of voxels.

7. The method of claim 1, wherein said generating further comprises generating a void alert signal upon determining that the tomogram has a void in the soil surrounding the corrugated pipe having a volume larger than a given volume threshold.

8. The method of claim 1, further comprising storing the inspection data on a computer-readable memory.

9. The method of claim 8, further comprising generating a tomogram based on the inspection data associated the voxels of the tomographic plane, the tomogram showing the integrity of a section of at least one of the corrugated pipe and the surrounding soil.

10. A Compton scattering (CS) inspection device for inspecting an infrastructure having a corrugated pipe, the corrugated pipe having a cylindrical wall being corrugated along a length thereof and forming a series of longitudinally extending corrugations, the CS inspection device comprising:
a frame adapted to be received against an inner face of the cylindrical wall and having a main axis;
a scanning plane parallel to an orientation of individual ones of the corrugations and intersecting the main axis;
a scanning module having an emitter of a beam of radiation particles and a detector of backscattered photons being mounted to the frame and being spaced apart from one another in the scanning plane; and
a control module operatively connected to the scanning module and configured to operate the emitter and the detector and to process inspection data received by the detector.

11. The CS inspection device of claim 10, wherein the emitter and the detector are spaced by a fixed spacing distance of about 15 cm or less.

12. A method of operating the CS inspection device of claim 11 for use in inspecting an infrastructure having a corrugated pipe, the corrugated pipe having a cylindrical wall being corrugated along a length thereof and forming a series of longitudinally extending corrugations, the method comprising the steps of:
determining a circumferential position and a longitudinal position associated with an area under test of an inner face of the cylindrical wall;
providing a support structure having first and second opposite support ends at the longitudinal position of the cylindrical wall;
positioning the first end of the support structure to the circumferential position and the second end of the support structure at a different circumferential position thereby; and
positioning the CS inspection device on the first end of the support structure and against the inner face of the cylindrical wall at the longitudinal and circumferential positions.

13. The method of claim 12, wherein the area under test is determined using at least one of a visual inspection and an acoustic inspection performed by a user.

14. The CS inspection device of claim 10, wherein the scanning module has a subframe slidably mounted to the frame via a rail assembly.

15. The CS inspection device of claim 14, wherein the rail assembly has a longitudinal guide rail parallel to the main axis and mounted to the frame, the subframe of the scanning device engaging into the longitudinal guide rail for sliding the scanning module therealong.

16. The CS inspection device of claim 10, wherein the emitter is pivotally mounted to the subframe of the scanning module via a pivot joint having a pivot axis perpendicular to the scanning plane.

17. The CS inspection device of claim 10, wherein the scanning module is pivotally mounted to the frame via a second pivot joint having parallel with the scanning plane.

18. The CS inspection device of claim 10, wherein the frame further comprises a support structure having two opposite support ends extending towards circumferentially different portions of the interior of the cylindrical wall, one of the two support ends being adapted to provide the frame against the inner face of the cylindrical wall.

19. The CS inspection device of claim 10, wherein the control module has a processor and a computer-readable memory useable to process and store the inspection data, and a power supply.

20. The CS inspection device of claim 19, wherein the power supply is a battery pack.

* * * * *